(12) United States Patent
Vaughan

(10) Patent No.: US 6,540,756 B1
(45) Date of Patent: Apr. 1, 2003

(54) PORTAL ACQUISITION TOOL

(76) Inventor: Thomas F. Vaughan, 122 Central Rd. #201, Indian Harbour Beach, FL (US) 32937

(*) Notice: Subject to any disclaimer, the term of this patent is extended or adjusted under 35 U.S.C. 154(b) by 0 days.

(21) Appl. No.: 09/529,895
(22) PCT Filed: Aug. 9, 1999
(86) PCT No.: PCT/US99/17975
  § 371 (c)(1),
  (2), (4) Date: Apr. 19, 2000
(87) PCT Pub. No.: WO00/10642
  PCT Pub. Date: Mar. 2, 2000

Related U.S. Application Data
(60) Provisional application No. 60/097,253, filed on Aug. 20, 1998.

(51) Int. Cl.[7] .............................................. A61B 17/00
(52) U.S. Cl. .......................... 606/116; 606/132; 40/300; 33/18.1; 33/27.03
(58) Field of Search ................................ 606/116, 132; 33/18.1–45, 483–500; 40/300–304

(56) References Cited

U.S. PATENT DOCUMENTS

| | | | |
|---|---|---|---|
| 1,382,271 A | 6/1921 | Cunningham | |
| D140,152 S | 1/1945 | Aichele | |
| 2,453,261 A | * 11/1948 | Peter | ............................ 33/490 |
| 2,500,873 A | 3/1950 | Sager | |
| 3,374,548 A | 3/1968 | Romney | |
| 3,502,070 A | 3/1970 | Bliss | |
| 4,279,259 A | 7/1981 | Lee | |
| 4,440,168 A | 4/1984 | Warren | |
| 4,506,676 A | 3/1985 | Duska | |
| 4,566,466 A | * 1/1986 | Ripple et al. | ............... 128/781 |
| 4,594,276 A | 6/1986 | Relyea | |
| 4,860,331 A | 8/1989 | Williams | |
| 5,232,452 A | 8/1993 | Russell | |
| 5,269,390 A | 12/1993 | Barrett | |
| 5,306,271 A | 4/1994 | Zinreich | |
| 5,407,440 A | 4/1995 | Zinreich | |
| 5,469,847 A | 11/1995 | Zinreich | |
| 5,615,485 A | * 4/1997 | Stoneberg | ................... 33/27.03 |
| 5,702,128 A | 12/1997 | Maxim | |
| 5,743,899 A | * 4/1998 | Zinreich | ......................... 606/1 |
| 6,175,760 B1 | * 1/2001 | Baskin et al. | ............... 600/436 |
| 6,197,034 B1 | * 3/2001 | Gvozdic et al. | ............. 606/116 |
| 6,253,771 B1 | * 7/2001 | McClain | ..................... 132/200 |

FOREIGN PATENT DOCUMENTS

GB  2 266 227 A  * 10/1993  ........... B43L/13/20

* cited by examiner

Primary Examiner—Linda C. M. Dvorak
Assistant Examiner—Ahmed Farah
(74) Attorney, Agent, or Firm—King & Schickli, PLLC

(57) ABSTRACT

A tool is provided for use in acquiring a treatment portal on the skin surface of a patient undergoing radiation therapy or the like. The portal acquisition tool includes a template portion having a cut-out pattern for marking the treatment portal on the skin and a handle portion which both facilitates use of the template and includes ruled markings for taking measurements. Additionally, the handle portion is provided with transverse lines for assisting the therapist in altering the source-to-skin distance during the administration of electron energy and an opaque backing which serves as a screen for reflecting the optical distance indicator projected by the linear accelerator.

17 Claims, 1 Drawing Sheet

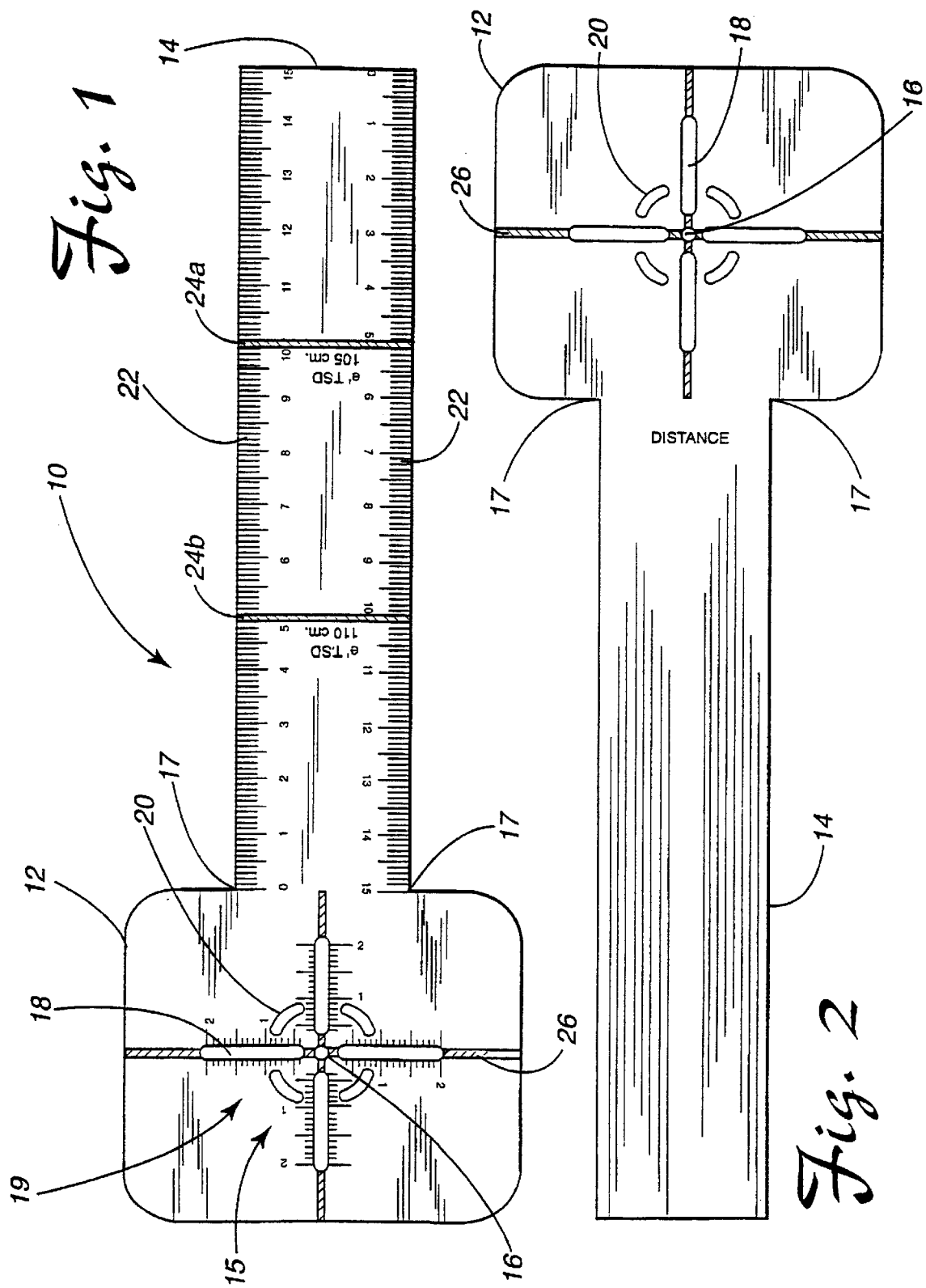

PORTAL ACQUISITION TOOL

This application claims the benefit of U.S. Provisional patent application Ser. No. 60/097,253, filed Aug. 20, 1998.

TECHNICAL FIELD

The present invention relates generally to the medical art and, more particularly, to a tool for assisting in accurately establishing and marking a treatment portal on the skin surface of a patient undergoing radiation therapy or the like.

BACKGROUND OF THE INVENTION

The administration of radiation energy is in widespread use as an effective means of treating malignant and benign conditions. Such radiation therapy is generally administered by large, complex machines called linear accelerators. Although the linear accelerators administer specific dosages of radiation to precise locations inside the human body, it must be realized that operation of these machines is highly dependent on human interaction to ensure that the treatment regimen is successful.

One important area where human interaction is necessary is in identifying the precise location on the skin surface of the patient where radiation must be administered to produce an effective treatment outcome. This area is commonly referred to as the treatment "portal." Prior to administering the actual radiation energy doses, it is first necessary for a team of scientists, including a treating oncologist and medical physicist, to view the internal anatomy of the patient and determine the precise locations where treatment is necessary. This is done when the patient is first brought in for radiation therapy by using a simulator, which is basically a scale model of the actual linear accelerator used during treatment without the radiation administering capabilities. To perform the simulation, the subject patient is laid on the treatment couch of the simulator below a gantry and raised vertically to the optimal imaging range. The oncologist and treating staff view the internal anatomy of the patient and locate the treatment site using fluoroscopy and reviewing pictures taken during internal imaging procedures, such as computerized axial tomography (CAT) scanning, magnetic-resonance imaging (MRI), or the like. The couch and gantry are movable to provide the oncologist with the best view of the anatomy he or she has determined needs treatment. Based on the positioning of the patient, who is normally laying down in a supine position, a sagittal laser is projected down the length of the patient's torso, a transverse laser is projected across the sagittal laser, and laterally extending lasers are projected running up and down the left and right sides of the body that intersect with the transverse laser. As any radiation therapist skilled in the art recognizes, the three areas where the lasers cross represent the triangulation points, which are marked. For some procedures, these triangulation points identify the treatment portals (i.e., the locations where radiation must be precisely administered to effectively eradicate a centralized diseased tissue mass), but it is also known to mark the triangulation points to ensure that the patient setup is the same for every treatment. For example, while a four field pelvic treatment will use triangulation points for both a setup point and a treatment portal, a two-field lung treatment would not but the lung still needs to be triangulated for accuracy and reproducibility.

Marking these locations with extreme precision is important, as small deviations from the treatment location can result in the irradiation of healthy tissue surrounding the targeted diseased tissue. In addition to failing to eradicate the diseased tissue, missing the target treatment area can result in the impairment of organs or other internal body structures, thus placing the already ill patient in perhaps a worse condition. Of particular concern is the use of such radiation near the spinal cord, where precision is especially critical, as any excessive or improper destruction of nerve tissue can result in severe paralysis.

To ensure that radiation is administered in a proper manner, professional medical practitioners known as radiation therapists or technologists are employed to, among other things, assist in designing, locating, and marking the treatment sites, or portals, on the skin surfaces on the body of the patient. To denote the treatment portal, conventional practice is to simply use a standard writing implement, such as a marker or pen, and draw the portal on the skin in a free-handed manner. Of course, it should be appreciated that such free hand markings are subject to variation based on application by different individuals, even when rulers or other conventional line drawing instruments are used. As imprecise lines can affect the course of treatment, a standard of quality assurance in applying such markings is desirable.

In an attempt to provide such precision portal markings, others have proposed the use of adhesive markers as an alternative to actually drawing the portal on the skin. For example, U.S. Pat. Nos. 5,306,271, 5,407,440, and 5,743,899, all to Zinreich et al. teach the use of various shapes and sizes of detachable, adhesive skin markers for placement at the treatment portal in place of the permanent tattoos that are presently used to permanently mark the center of the portal. Although such adhesive markers ostensibly provide greater precision than the conventional method of freehanded drawing described above, several limitations remain. First of all, radiation therapy patients generally undergo a multiple stage regimen of treatment sessions which can occur over the course of several days or even weeks. The light duty, skin-safe adhesives proposed in the above-referenced patents simply do not stay in place over the course of an extended treatment session. If an adhesive marker inadvertently falls from the predetermined treatment location, it is necessary to carefully reapply the marker or, if no permanent mark was made on the skin, to revisit the simulator for relocation of the treatment portal. Of course, this results in a waste of resources and additional discomfort for the patient.

Additionally, such markers are particularly troublesome for patients with excessive amounts of body hair or where sweat and other fluids can come into contact with and degrade the adhesive, which of course weaken the ability of the marker to remain adhered on the body. Again, if the marker is inadvertently removed, re-application or re-simulation becomes necessary, which as noted above results in a significant waste of valuable professional time and also serves to extend the already uncomfortable experience of the patient undergoing therapy.

The troublesome nature of these adhesive markers is explicitly recognized in the most recently issued '899 patent, which proposes the improvement of imbuing the adhesive backing with transferable ink. This ink is supposed to transfer to the skin at some finite time after application of the marker, thereby providing a landmark that facilitates replacement if inadvertent detachment occurs. It must be appreciated that even with the use of such ink imbued markers, limitations still remain. First of all, the markers do not eliminate the requirement of locating the central axis point of the treatment portal on the body of the patient. Precisely placing the marker oversuch an axis is difficult and may require several attempts to achieve the proper positioning. In addition, the ink blot provided by the backing simply cannot define the portal with the precision necessary for an accurate treatment regimen. Also, where excessive hair or sweat is present, the ink may not sufficiently penetrate the skin to leave a readily distinguishable mark. Finally, as with all the adhesive markers, the use of multiple markers to define a treatment portal is time consuming. The excessive application time and associated cost is simply not worth the limited benefit provided by such adhesive markers.

Thus, a need is identified for a device that facilitates the precise marking of a treatment portal upon the skin surface of a patient undergoing radiation therapy or a similar procedure. The device would be of simple construction and, thus, easy and inexpensive to manufacture. Moreover, the device would include a variety of ruled markings which both assist the radiation therapist in locating and drawing the treatment portal, as well as shifting the portal if the treatment location varies. Additionally, the use of the device as a light shield for locating and viewing the radiation field margins or optical distance indicator projected by the simulator would also be possible. Overall, the device would ease the burdens on radiation therapists to precisely mark treatment portals and improve the entire treatment regimen.

SUMMARY OF THE INVENTION

Accordingly, it is a primary object of the present invention to provide a tool or device that assists a radiation therapist or the like in precisely establishing, or acquiring, and marking a treatment portal on the skin surface of a patient undergoing radiation therapy.

Another object of the present invention is to provide a portal acquisition tool having a template portion with a cut-out pattern for receiving a writing implement or the like, said cut-out pattern including a center aperture and a plurality of cross-hair slits surrounding said aperture to permit the precision marking of the treatment portal.

Still a more specific object of the present invention is to provide a portal acquisition tool wherein the template portion includes a center aperture for marking an isocenter axis, laser acquisition lines for assisting in aligning the portal acquisition tool along the laser lines, opposed pairs of cross-hair slits for marking focus lines along the projecting laser lines, and an arcuate slit extending between each adjacent pair of cross-hair slits for marking lines that denote the presence of an active treatment portal.

Yet another object of the present invention is to provide a portal acquisition tool including a handle portion, said handle portion having ruled markings for assisting a radiation therapist in determining the location of a treatment portal and shifting the location of the portal, if necessary.

A further object of the present invention is to provide a portal acquisition tool having an opaque backing which provides a screen for reflecting light, such as that projected from an optical distance indicator on a linear accelerator or the light indicating the margin of a radiation field during treatment.

Still a further object of the present invention is to provide a portal acquisition tool which includes means for assisting a therapist in determining an optimum target to skin distance for administering electron energy.

Yet a further object of the present invention is to provide a portal acquisition tool including a head portion having at least one corner that facilitates the tracing of the light field corners defining the treatment portal.

Additional objects, advantages and other novel features of the invention will be set forth in part in description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a novel device is provided for use by a radiation therapist to establish and mark, or collectively "acquire," a treatment portal on the skin surface of a patient undergoing radiation therapy or a similar treatment regimen. Advantageously, the portal acquisition tool, or PAT, is designed to permit a radiation therapist to precisely mark treatment portals in an easy and efficient manner by substantially eliminating the unacceptable and imprecise markings associated with the conventional practice of free-hand drawing. As will be appreciated upon reviewing the disclosure which follows, numerous advantages will inure to the benefit of the patient from the use of the portal acquisition tool described herein by the skilled radiation therapist.

In the preferred embodiment, the portal acquisition tool (PAT) is formed having a substantially planar body that includes a template or head portion and a handle portion, both of which provide the tool with a number of features that are useful in administering radiation, electron energy, or similar therapy regimens. Preferably, the template portion or head of the tool is substantially square and includes 90° corners at the interface with the handle portion that facilitate the tracing of the corners of the light field that define the treatment portal. A center aperture forms a part of this template portion and permits the therapist to mark an isocenter axis, which is the exact intersection of the laser lines on the skin surface of the patient. Surrounding this center aperture are one or more cross-hair slits which guide the therapist in drawing lines on the skin to focus on the isocenter marker. Preferably, the cross-hair slits are provided in pairs which emanate orthogonally from the isocenter axis marker. It is also preferred that the cross-hair slits are formed as distinct from the center aperture, thereby ensuring that the focus lines cannot cross through the isocenter mark. However, it is within the broadest aspects of the present invention to make the aperture and cross-hair slits coterminous. In addition, an optional arcuate slit may be provided which extends between each adjacent pair of cross-hair apertures. The arcuate slits advantageously permit the isocenter marker to be surrounded by substantially circular marker segments which denote the presence of an active treatment portal, as opposed to a set-up point.

As should now be appreciated, after the treatment portals are properly marked during simulation and accepted by the treating oncologist as accurate, the center axis is tattooed onto the skin of the patient to leave a permanent record of the isocenter axis. To ensure that the tattooing is completed in a satisfactory manner, the portal markings previously drawn are wiped off using an alcohol pad. After it is determined that the tattoo is properly positioned, the PAT is advantageously utilized to easily and efficiently reapply the cross-hair and arcuate lines which serve to re-define the treatment portal. Furthermore, if the lines deteriorate after bathing or rubbing against clothing, the PAT permits the easy, efficient, and most importantly, precise re-application of the lines for use in further treatment sessions. No troublesome re-application of adhesive stickers over faded or substantially invisible marker points is necessary.

In accordance with another important aspect of the present invention, the cross-hair slits are also provided with ruled markings. These markings assist the therapist in "shifting," or moving, the central axis if the preferred treatment site is changed during the procedure. The cross-hair slits in the preferred embodiment of the PAT are roughly one to one-and-one-half centimeters in length and, therefore, with a small allowance for a gap for dividing the isocenter axis aperture from the slits, if present, the marks preferably are made from approximately the 4 millimeter mark to a 2.0 centimeter mark.

Use of the PAT is facilitated by an elongate handle which extends from the template or head portion of the tool. In the preferred embodiment, the handle is provided with a series of ruled markings along both peripheral edges. These ruled markings are useful in determining portal locations, as well as performing central axis shifts and measuring gap calculations for abutting fields. In the preferred embodiment, fifteen centimeter markings are provided along each edge, although it should be appreciated that the length may be increased or decreased or the marking intervals altered without deviating from the principles of the present invention.

In accordance with yet another important aspect of the present invention, the handle portion of the PAT is also provided with markers for making adjustments to the preferred distance for the administration of electron energy. It is known in the art that the preferred target-to-skin distance (TSD) for the administration of electron energy is approximately 100 centimeters. However, due to variations in patient anatomy or treatment field sizes, it is often necessary to extend the treatment distance an additional five or ten centimeters. To facilitate extending the TSD, transverse electron laser acquisition lines are provided at five and ten centimeter intervals along the upper surface of the handle portion of the PAT. By aligning the patient with the sagittal laser at the 100 centimeter mark, the electron laser acquisition lines easily allow the therapist to shift the TSD five or ten centimeters, as necessary, to achieve the optimum results. The medical physicist may then calculate the treatment dose of energy at the extended distance as easily as if it were being administered at the optimal distance of 100 centimeters.

In accordance with still another important aspect of the present invention, the surface of the handle portion opposite the ruled markings and electron laser acquisition lines is opaque. This permits the radiation therapist to use the backside of the PAT as a screen to reflect the optical distance indicator, which is projected from the machine head of the linear accelerator and appears as a light on the skin surface of the patient. This is particularly advantageous where light-skinned or obese patients are presented, as the skin color or contours often make it difficult to see the projected scale.

Yet another advantage of the PAT is that the template or head portion may also be opaque and used to reflect light, such as that projected from the simulator and used to determined the margin of radiation field for portions of the body capable of projecting a shadow, such as breasts. Thus, by placing the head of the tool behind a breast or similar object, a shadow is projected that assists the technologist in evaluating the margin of the radiation field and developing a proper treatment regimen.

Still other objects of the present invention will become apparent to those skilled in this art from the following description wherein there is shown and described a preferred embodiment of this invention, simply by way of illustration of one of the modes best suited to carry out the invention. As will be realized, the invention is capable of other, different embodiments and its several details are capable of modification in various, obvious aspects without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention and, together with the description, serve to explain the principles of the invention. In the drawings:

FIG. 1 is a top plan view of the portal acquisition tool of the present invention, including the template portion having a central aperture and a plurality of slits which facilitate the acquisition of a treatment portal and the multi-functional handle portion;

FIG. 2 is a bottom plan view of the portal acquisition tool of the present invention constructed identical to the device shown in FIG. 1.

Reference will now be made in detail to the present preferred embodiment of the invention, an example of which is illustrated in the accompanying drawings.

DETAILED DESCRIPTION OF THE INVENTION

Reference is now made to FIG. 1 of the drawings, which show a preferred embodiment of a portal acquisition tool (PAT) 10 constructed in accordance with the principles of the present invention. As illustrated, the PAT 10 includes a head or template portion 12 and an elongate handle portion 14. As will be described in more detail below, the template portion 12 is provided with a cutout pattern 15 for facilitating the marking of a treatment portal on the skin surface of a patient undergoing radiation therapy, while the handle portion 14 is provided with markings to assist the radiation therapist in performing other duties related to portal marking and the administration of photon and electron energy. Together, the benefits provided for the first time by this simple device serve to significantly enhance the precision and accuracy with which treatment is provided to patients undergoing radiation therapy regimens.

The head portion 12 is substantially rectangular and thus, forms 90° corners 17 at the transition with the handle that assist in marking or tracing the corners of the light field that defines the location of the treatment portal. At the center or the head portion 12 is a cut out pattern, including a central aperture 16. The center aperture 16 permits the marking of the central axis, or isocenter, which establishes the center of the treatment portal. Radiating outwardly along perpendicular axes extending through the center aperture 16 are pairs of opposed cross-hair slits 18 for marking lines which focus on the center aperture. It should be appreciated that the center aperture 16 and cross-hair slits 18 are shown as being distinct, but it is within the broadest aspects of the invention to make them both coterminous. Additionally, as described further below, surface indicia 26, termed laser acquisition lines, are provided for assisting in lining up the PAT with the laser lines crossing on the body of the patient.

Ruled markings 19 are provided adjacent to each of the slits 18 for assisting the therapist in shifting the location of the treatment port, if necessary. If material is presented between the center aperture 16 and each of the cross-hair slits 18, the ruled markings preferably begin at approximately 4 millimeters and extend to 2.0 centimeters. Of course, varying the units of the markings or the dimensions of the slits 18 is possible without departing from the principles of the present invention.

An arcuate slit 20 is formed and extends between each pair of adjacent cross-hair slits 18. It should be appreciated that collectively, the arcuate slits 20 permit the marking of a substantially circular, but segmented pattern, around the center aperture 18. As is known in the art, this marking is done to denote the presence of an active treatment portal, as opposed to a set-up point.

Extending from the template portion 12 is a handle portion 14. The handle portion 14 is preferably elongated, thereby allowing the therapist using the PAT 10 to easily grasp and move the template portion 12 into the desired position for marking the treatment portal. In the preferred embodiment, as shown in FIG. 1, the upper surface of the handle portion 14 is provided with mirrored ruled markings 22 along both peripheral edges. These ruled markings 22 assist the therapist in taking measurements on the body of the patient to determine the precise locations for treatment, and as described further below, may also assist in shifting the treatment ports, if necessary. For purposes of illustration, the ruled markings 22 are shown as fifteen centimeter markers, although it should be appreciated that the use of different units and longer or shorter scales is possible. In addition to the ruled markings 22, the handle portion 14 is provided with transverse electron laser acquisition lines 24a, 24b that are useful in adjusting the optimum target-to-skin distance during the administration of electron energy therapy, as described further below.

As illustrated in FIG. 2, the lower surface, or underside, of the handle portion 14 is preferably opaque, and most preferably white. This opaqueness advantageously permits use of the PAT 10 as a screen to reflect light from the optical distance indicator (ODI) of the linear accelerator that is projected onto the skin surface of the patient. This feature is of particular benefit where light-skinned or obese patients are presented, as the light may be difficult to see due to absorption or contouring, respectively. As further illustrated in FIG. 2, the underside of the head portion 12 of the PAT is also preferably opaque, and most preferably white. This white surface permits use of the tool in ensuring that an adequate margin of radiation field exists over protruding portions of the body, such as breasts.

The multi-functional aspects and concomitant advantages arising from use of the PAT 10 will now be described in detail. In the primary use in marking treatment portals, the handle portion 14 of the PAT 10 is grasped by the therapist and held at the triangulation points where the sagittal/transverse and left and right lateral/transverse lasers intersect. With the assistance of the laser acquisition lines 26 and the cross-hair slits 18, the precise crossing of the lasers is located in the center aperture 16 and noted using a marking implement, such an ink pen or the like. Moreover, as shown in FIGS. 1 and 2, the template is provided with indicia 26 for assisting in lining up the crossing laser lines. After alignment is achieved, the cross-hair slits 18 are filled in along the laser lines. If the portal is for actual treatment, and not merely a set-up point, the arcuate apertures 20 are also marked. The substantially 90° angles formed by the corners 17 where the head portion 12 meets the handle portion 14 are then used to trace the corners of the light field to fully define the treatment portal. As should now be appreciated, the PAT 10 permits a therapist to easily, efficiently, and most importantly, precisely, mark and denote the treatment portals on the body of the patient.

Another important feature of the PAT 10 is the presence of ruled markings 19 adjacent to the cross-hair slits 18. In the case of conedowns or boosts, these markings 19 permit the therapist to double-check the digital readouts of the linear accelerator by actually measuring the distances on the body to the newly established treatment location. Also, the ruled markings 19 assist in moving the isocenter marker itself, without the aid of the simulator, if necessary for shifting the treatment portal.

Yet another important feature of the PAT 10 is the presence of the transverse electron laser acquisition lines 24a, 24b to permit the determination of the preferred target-to-skin distance (TSD) for the administration of electron energy. By aligning the patient with the sagittal laser at the 100 centimeter mark, the electron laser acquisition lines 24a, 24b permit the distance to be shifted five or ten centimeters, as necessary, to achieve the optimum target-to-skin distance. More specifically, if the TSD must be adjusted from the preferred 100 centimeters to 105 centimeters due to variations in patient anatomy or treatment field sizes, the first transverse electron laser acquisition line 24a is used by the therapist to extend the distance. Similarly, if the desired extension is from 100 to 110 centimeters, the second electron laser acquisition line 24b is used. The medical physicist may then calculate the treatment dose of energy at the extended distance as easily as if it were being administered at the optimal distance of 100 centimeters.

Preferably, the PAT 10 is formed from a lightweight, but durable, plastic material, with the template portion 12 ideally being white or provided with light coloring to permit easy viewing for therapists in the darkened or low-light conditions typically presented in the treatment and simulation rooms. The handle portion 14 is formed of a similar plastics material and is provided with an opaque backing or formed with an opaque insert, which serves as the screen for the optical distance indicator (ODI). Although plastics materials are preferred as being inexpensive, flexible, and durable, it should also be appreciated that a number of other materials may be used without deviating from the principles of the present invention, such as wood, metal, or the like.

Other possible modifications include altering the dimensions of the cross-hair 18 and arcuate slits 20, which are shown as being a particular size and shape in FIGS. 1 and 2 for purposes of illustration only. For example, an adjustment is possible to make the arcuate slits 20 occupy a smaller segment of the arc between the adjacent cross-hair slits 18. Likewise, it is possible to move the arcuate slits 20 radially toward or away from the center aperture 16 without altering the ability of the PAT to mark the portal as active, or to provide multiple sets of arcuate slots. In short, the slits 18, 20 are capable of numerous modifications without deviating from the principles of the present invention.

In summary, a tool 10 is provided for use by radiation therapists or the like in acquiring the precise location of a treatment portal on the skin surface of a patient. The portal acquisition tool 10 includes a head or template portion 12 having a cut-out pattern for marking the treatment portal on the skin and a handle portion 14 which both facilitates use of the template and includes ruled markings for taking measurements (FIG. 1). The cut-out pattern of the template portion includes a center aperture 16 for marking an isocenter axis, opposed pairs of cross-hair slits 18 for drawing lines which focus on the center aperture 16, and arcuate slits 20 extending between the cross-hair slits 18 which may be used to denote the presence of an active treatment portal. The head portion 12 is substantially rectangular and includes 90° corners that assist in tracing the corners of the light field during simulation. Additionally, the handle portion 14 is provided with transverse electron laser acquisition lines 24a, 24b for assisting the therapist in altering the target-to-skin distance (TSD) during the administration of electron energy and a white backing which serves as a screen for reflecting the optical distance indicator (ODI) projected by the linear accelerator. The head of the tool 10 may also be used to reflect light to indicate that an adequate margin of radiation field is provided over protruding portions of the body, such as breasts.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A tool for assisting in establishing triangulation points or a treatment portal on a skin surface of a patient undergoing radiation therapy, said tool comprising:
   a generally planar body including a template portion having an aperture, a plurality of cross-hair slits, and a plurality of arcuate slits extending between said cross-hair slits formed therein,
   whereby said aperture and said cross-hair and arcuate slits are used for accurately marking the triangulation points or treatment portal.

2. The tool according to claim 1, wherein said template portion further includes surface indicia positioned adjacent to said cross-hair slits for assisting in aligning said tool.

3. The tool according to claim 1, wherein ruled markings are provided adjacent to each of said plurality of cross-hair slits, whereby said ruled markings assist in shifting the location of the triangulation points or treatment portal.

4. The tool according to claim 1, wherein a first planar surface of said template portion is opaque, whereby said template portion can be used to determine whether an adequate margin of radiation field is provided during treatment.

5. The tool according to claim 1, wherein said template portion includes at least one corner that is substantially 90° for tracing a corner of the treatment portal.

6. The tool according to claim 1, wherein said planar body further includes an elongate handle portion.

7. The tool according to claim 6, wherein a first planar surface of said handle portion is provided with ruled markings, whereby said ruled markings facilitate the taking of measurements to accurately locate or move the triangulation points or treatment portal.

8. The tool according to claim 7, where a second planar surface of said handle portion opposite said ruled first planar surface is generally opaque, whereby said opaque surface serves as a screen for receiving and reflecting light.

9. The tool according to claim 7, wherein a first planar surface of said handle portion is provided with a plurality of transversely extending electron laser acquisition lines, whereby said lines assist in determining an optimum target to skin distance for providing treatment using electron energy.

10. A portal acquisition tool for use in accurately determining triangulation points or a treatment portal location on a skin surface of a patient, said portal acquisition tool comprising:
    a template having a center aperture for marking an isocenter axis, a plurality of cross-hair slits for marking focus lines emanating from said center aperture, and a plurality of arcuate slits for assisting in defining the treatment portal, each of said slits extending between a pair of said plurality of cross-hair slits; and
    a handle extending from said template for facilitating the accurate placement of said template over the triangulation point or treatment location on the skin surface of the patient.

11. The portal acquisition tool according to claim 10, wherein said handle includes a first surface and a second surface,
    said first surface having ruled markings for assisting in determining the triangulation points or treatment portal location; and
    said second surface being substantially opaque for reflecting light.

12. The portal acquisition tool according to claim 11, wherein said second surface of said handle further includes a plurality of transverse electron laser acquisition lines, whereby said lines assist in determining an optimum target to skin distance for the treatment of disease using electron energy.

13. The portal acquisition tool according to claim 10, wherein ruled markings are provided along each of said cross-hair slits.

14. A method of marking a treatment portal or triangulation point on the body of a patient undergoing radiation therapy, comprising the steps of:
    positioning a template having a cutout pattern including at least one cross-hair slit over the body of the patient;
    aligning the cross hair slit with a light projected on the body identifying the treatment portal or triangulation point; and
    physically contacting the body with a marker through the cross-hair slit to deposit a semi-permanent indication of the location of the treatment portal or triangulation point on the body.

15. The method according to claim 14, wherein the light source is a laser projecting from a linear accelerator simulator and the step of positioning the template further includes aligning the at least one cross-hair slit on the template with the laser.

16. The method according to claim 14, wherein at least one side of said template is opaque, said method further including using said opaque side of said template to serve as a screen for reflecting light and to determine whether an adequate margin of radiation field is provided during treatment.

17. The method according to claim 14, wherein said template includes a handle and said positioning step is manually completed using said handle.

* * * * *